(12) United States Patent
Ohri et al.

(10) Patent No.: US 8,440,309 B2
(45) Date of Patent: May 14, 2013

(54) CROSSLINKED POLYMERS WITH THE CROSSLINKER AS THERAPEUTIC FOR SUSTAINED RELEASE

(75) Inventors: Rachit Ohri, Framingham, MA (US);
Phillip Blaskovich, Salem, MA (US);
Joshua Kennedy, Somerville, MA (US);
Steven L. Bennett, Cheshire, CT (US);
Arthur Driscoll, Reading, MA (US)

(73) Assignees: Confluent Surgical, Inc., Bedford, MA (US); Covidien LP, Mansfield, MA (US)

( * ) Notice: Subject to any disclaimer, the term of this patent is extended or adjusted under 35 U.S.C. 154(b) by 0 days.

(21) Appl. No.: 13/017,287

(22) Filed: Jan. 31, 2011

(65) Prior Publication Data

US 2012/0197028 A1  Aug. 2, 2012

(51) Int. Cl.
*B32B 27/28* (2006.01)
*A61K 47/30* (2006.01)

(52) U.S. Cl.
USPC ........................................ 428/423.1; 514/773

(58) Field of Classification Search . 428/423.1; 514/773
See application file for complete search history.

(56) References Cited

U.S. PATENT DOCUMENTS

| | | | |
|---|---|---|---|
| 4,179,337 A | 12/1979 | Davis et al. | |
| 5,122,614 A | 6/1992 | Zalipsky | |
| 5,342,940 A | 8/1994 | Ono et al. | |
| 5,428,128 A | 6/1995 | Mensi-Fattohi et al. | |
| 5,539,063 A | 7/1996 | Hakimi et al. | |
| 5,559,213 A | 9/1996 | Hakimi et al. | |
| 5,595,732 A | 1/1997 | Hakini et al. | |
| 5,648,506 A | 7/1997 | Desai et al. | |
| 5,747,646 A | 5/1998 | Hakimi et al. | |
| 5,780,578 A | 7/1998 | Mashelkar et al. | |
| 5,792,834 A | 8/1998 | Hakimi et al. | |
| 5,834,594 A | 11/1998 | Hakimi et al. | |
| 5,849,860 A | 12/1998 | Hakimi et al. | |
| 5,932,462 A | 8/1999 | Harris et al. | |
| 6,258,351 B1 | 7/2001 | Harris | |
| 6,362,254 B2 | 3/2002 | Harris et al. | |
| 6,432,397 B1 | 8/2002 | Harris | |
| 6,437,025 B1 | 8/2002 | Harris et al. | |
| 6,514,534 B1 | 2/2003 | Sawhney | |
| 6,515,100 B2 | 2/2003 | Harris | |
| 6,541,015 B2 | 4/2003 | Bentley et al. | |
| 6,541,543 B2 | 4/2003 | Harris et al. | |
| 6,552,167 B1 | 4/2003 | Rose | |
| 6,558,658 B2 | 5/2003 | Harris | |
| 6,566,406 B1 | 5/2003 | Pathak et al. | |
| 6,605,294 B2 | 8/2003 | Sawhney | |
| 6,703,047 B2 | 3/2004 | Sawhney et al. | |
| 6,818,018 B1 | 11/2004 | Sawhney | |
| 7,009,034 B2 | 3/2006 | Pathak et al. | |
| 7,018,624 B2 | 3/2006 | Harris | |
| 7,049,285 B2 | 5/2006 | Park | |
| 7,329,516 B2 | 2/2008 | Li et al. | |
| 7,347,850 B2 | 3/2008 | Sawhney | |
| 7,432,330 B2 | 10/2008 | Kozlowski et al. | |
| 7,432,331 B2 | 10/2008 | Kozlowski et al. | |
| 2001/0007765 A1 | 7/2001 | Harris et al. | |
| 2001/0027212 A1 | 10/2001 | Bentley et al. | |
| 2002/0064546 A1 | 5/2002 | Harris | |
| 2004/0076602 A1 | 4/2004 | Harris | |
| 2004/0086479 A1 | 5/2004 | Grinstaff et al. | |
| 2004/0131582 A1 | 7/2004 | Grinstaff et al. | |
| 2008/0114092 A1 | 5/2008 | Sawhney | |
| 2008/0241102 A1 | 10/2008 | Hersel et al. | |
| 2010/0291021 A1 | 11/2010 | Vetter et al. | |

FOREIGN PATENT DOCUMENTS

| | | |
|---|---|---|
| EP | 0 473 268 | 3/1992 |
| EP | 0 841 360 | 5/1998 |
| EP | 2 143 737 A1 | 1/2010 |
| EP | 2 196 193 A1 | 6/2010 |
| EP | 2 233 160 A2 | 9/2010 |
| EP | 2 233 161 A2 | 9/2010 |
| WO | 92/00748 | 1/1992 |
| WO | WO 02/102864 A1 | 12/2002 |
| WO | WO 2007/098466 A2 | 8/2007 |
| WO | WO 2010/019233 A1 | 2/2010 |

OTHER PUBLICATIONS

Jin et al. (CAPLUS Abstract of CN 101104078).*
International Search Report issued in Application EP 11250562.3 mailed Dec. 8, 2011.
International Search Report issued in Application EP 11250564.9 mailed Dec. 8, 2011.
International Search Report issued in Application EP 11250563.1 mailed Dec. 27, 2011.
International Search Report issued in Application EP 11250566.4 mailed Dec. 22, 2011.
International Search Report issued in Application EP 11250565.6 mailed Dec. 23, 2011.
European Search Report for EP 12152996.0-1216 date of completion is Jun. 12, 2012 (7 pages).
Jo Seongbong et al.: "Modification of oligo(poly(ethylene glycol) fumarate) macromer with a GRGD peptide for the preparation of functionalized polymer networks", Biomacromolecules, American Chemical Society; US., vol. 2, No. 1, Apr. 1, 2001, pp. 255-261, XP002441776, ISSN: 1525-7797, DOI: 10.1021/BM000107E * figure 1 *.

* cited by examiner

*Primary Examiner* — Robert Havlin

(57) ABSTRACT

Crosslinked polymers, methods for their preparation and use, are described in which the crosslinked polymers are formed from at least two polymer precursors, one of which is designed, upon degradation of the crosslinked polymer, to release the second polymer precursor in its original, unmodified chemical form.

6 Claims, 2 Drawing Sheets

CROSSLINKED POLYMERS WITH THE CROSSLINKER AS THERAPEUTIC FOR SUSTAINED RELEASE

BACKGROUND

1. Technical Field

The present disclosure relates generally to crosslinked polymers formed from at least two precursors, and more particularly to crosslinked polymers where the crosslinker or one of the precursors is a therapeutic agent which can be released in its original, unmodified form upon degradation of the polymer material. Methods of preparing and uses for such crosslinked polymers are also described.

2. Background of Related Art

In the field of medicine there has been a growing recognition of the benefits of using crosslinked polymers and biomaterials for the treatment of local diseases. Local diseases are diseases that are manifested at local sites within the living animal or human body, for example atherosclerosis, postoperative adhesions, rheumatoid arthritis, cancer, and diabetes. Crosslinked polymers may be used in drug and surgical treatments of such diseases.

Historically, many local diseases have been treated by systemic administration of drugs. In this approach, in order to achieve therapeutic levels of drugs at local disease sites, drugs are delivered (via oral administration or injection) at a high systemic concentration, often with adverse side effects. As an alternative, locally implanted crosslinked polymers or biomaterials may be used as carriers to deliver drugs or therapeutic agents to local sites within the body, thereby reducing the need for the systemic administration of high concentrations of such drugs or therapeutic agents.

However, upon degradation of such locally implanted crosslinked polymers or biomaterials, the drug or therapeutic agent may be released as a modified molecule. Although the release of a modified drug molecule may provide some therapeutic effect, it would be beneficial to provide crosslinked polymers or biomaterials which upon degradation, release a drug or therapeutic agent in its original, unmodified form, e.g., without end-capping, which may maximize the therapeutic effect of the agent.

Moreover, if a precursor of the polymer or biomaterial is itself the therapeutic agent [e.g., the crosslinking agent], then the mechanism of sustained local release is built into the implanted crosslinked polymer or biomaterial. As the crosslinked polymer degrades over time, the therapeutic agent will be released in a sustained manner.

SUMMARY

Accordingly, the present disclosure describes crosslinked polymers or biomaterials formed from at least two precursors, wherein at least one of the precursors is a therapeutic agent which can be released in an unmodified form upon degradation of the crosslinked polymer or biomaterial. Methods of forming such crosslinked polymers and methods of local delivery of at least one therapeutic agent are also described herein.

In embodiments, a first polymer precursor is described comprising a formula

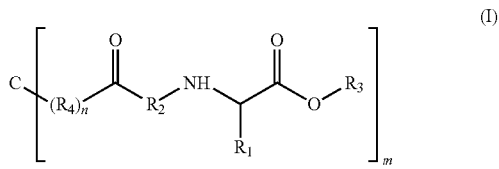

wherein $1 \leq n \leq 500{,}000$, and $m \geq 1$;
C=represents a core molecule;
$R_1$=—H, or an amino acid side chain;
$R_2$=an alkyl group, a substituted or unsubstituted aryl group, or a peptide;
$R_3$=an electrophilic functional group, a nucleophilic functional group, or a group that allows for polymer crosslinking reaction(s); and
$R_4$=a water-soluble repeat structure or unit of a polymer backbone, or an enzymatically cleavable repeat structure or unit of a polymer backbone.

In certain embodiments, a first polymer precursor is a structure which includes a water-soluble group derived from polyethylene glycol (PEG). For example, a first polymer precursor is described comprising a formula

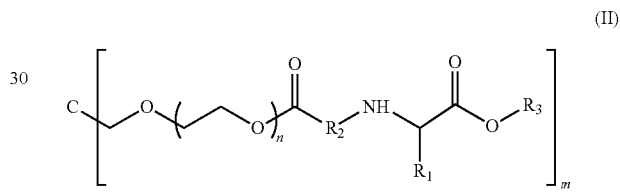

wherein $1 \leq n \leq 500{,}000$, and $m \geq 1$;
C=represents a core molecule;
$R_1$=—H, an amino acid side chain;
$R_2$=an alkyl group, a substituted or unsubstituted aryl group, or a peptide; and
$R_3$=an electrophilic functional group, a nucleophilic functional group, or a group that allows for polymer crosslinking reaction(s).

In embodiments, the first polymer precursor may be combined with a second polymer precursor or crosslinker which includes pendant complimentary reactive groups capable of interacting with $R_3$ of the first polymer precursor to form the crosslinked polymers described herein.

Methods of preparing crosslinked polymers are also described. For instance, one method of preparation includes combining a first polymer precursor comprising a formula

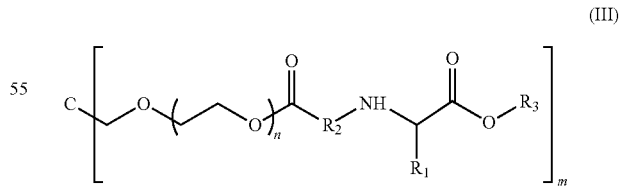

wherein $1 \leq n \leq 500{,}000$, and $m \geq 1$;
C=represents a core molecule;
$R_1$=—H, or an amino acid side chain;
$R_2$=an alkyl group, a substituted or unsubstituted aryl group, or a peptide;
$R_3$=an electrophilic functional group;
with a second polymer precursor comprising pendant nucleophilic functional groups.

In another example, a method of preparing crosslinked polymers includes combining a first polymer precursor comprising a formula

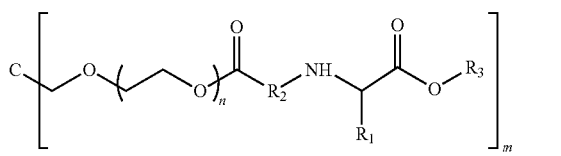

(IV)

wherein 1≦n≦500,000, and m≧1;
C=represents a core molecule;
$R_1$=—H, or an amino acid side chain;
$R_2$=an alkyl group, a substituted or unsubstituted aryl group, or a peptide;
$R_3$=a nucleophilic functional group;
with a second polymer precursor comprising pendant electrophilic functional groups.

The first and second polymer precursors may initially be combined in a solid or liquid state.

DETAILED DESCRIPTION

Figure 1:
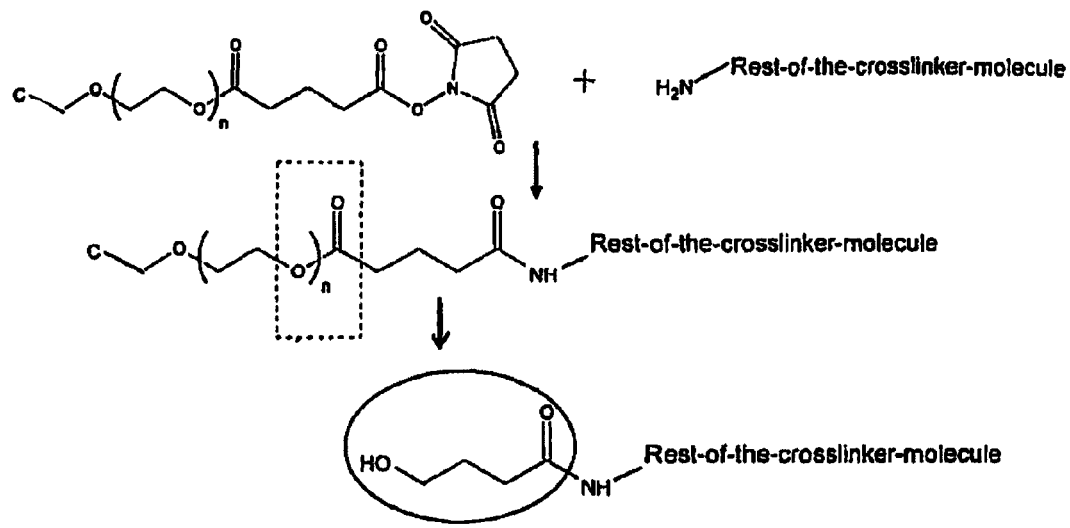
FIG. 1 illustrates the polymerization chemistry of combining first and second polymer precursors to form a crosslinked polymer and the degradation of the crosslinked polymer.

The novel crosslinked polymers described herein may be formed from the reaction of at least two polymer precursors having electrophilic and nucleophilic functional groups. The polymer precursors may be non-toxic and biologically acceptable.

In embodiments, a first polymer precursor displaying the following general formula (I):

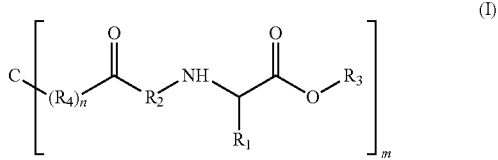

(I)

wherein 1≦n≦500,000, and m≧1;
C=represents a core molecule;
$R_1$=—H, an amino acid side chain;
$R_2$=an alkyl group, a substituted or unsubstituted aryl group, or a peptide;
$R_3$=an electrophilic functional group, a nucleophilic functional group, or a group that allows for polymer crosslinking reaction(s); and
$R_4$=a water-soluble repeat structure or unit of a polymer backbone, or an enzymatically cleavable repeat structure or unit of a polymer backbone
may be combined with a second polymer precursor having pendant complimentary reactive groups capable of interacting with $R_3$ of the first polymer precursor of formula I to form the crosslinked polymers described herein. In some embodiments, both the first and second polymer precursors may be made following formula I.

The first polymer precursors described in formula I includes a polymer repeat unit which may be a water-soluble group ($R_4$). Suitable water soluble groups ($R_4$) may be derived from, in whole or in part, any of the following: polyethers, for example polyalkylene oxides such as polyethylene glycol ("PEG"), polyethylene oxide ("PEO"), polyethylene oxide-co-polypropylene oxide ("PPO"), co-polyethylene oxide block or random copolymers, and polyvinyl alcohol ("PVA"); poly(vinyl pyrrolidinone) ("PVP"); poly(amino acids); dextran and the like. The polyethers and more particularly poly(oxyalkylenes) or poly(ethylene oxide) or polyethylene oxide are useful.

In embodiments, a first polymer precursor may be a structure which includes a water-soluble group derived from polyethylene glycol (PEG), as shown in the following general formula (II):

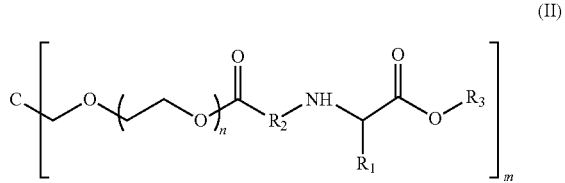

(II)

wherein 1≦n≦500,000, and m≧1;
C=represents a core molecule;
$R_1$=—H, or an amino acid side chain;
$R_2$=an alkyl group, a substituted or unsubstituted aryl group, or a peptide; and
$R_3$=an electrophilic functional group, a nucleophilic functional group, or a group that allows for polymer crosslinking reaction(s).

may be combined with a second polymer precursor having pendant complimentary reactive groups capable of interacting with $R_3$ of the first polymer precursor to form the crosslinked polymers described herein. For example, in some embodiments, $R_3$ may represent nucleophilic groups and the second polymer precursor may include complimentary electrophilic groups suitable for reaction or crosslinking with the nucleophilic groups of the first polymer precursor. In some embodiments, the second polymer precursor may be referred to as a "crosslinker". In embodiments, a crosslinker is a polymer precursor which lacks repeating units. Upon degradation of such crosslinked polymers, the crosslinker may be released in its original, unmodified form.

In certain embodiments one of the polymer precursor or crosslinker may be a therapeutic agent, which upon degradation of the crosslinked polymer, is released in its original, unmodified form.

Each of the polymer precursors may be multifunctional, meaning that the precursors may comprise two or more electrophilic and/or nucleophilic functional groups, such that a nucleophilic functional group on one polymer, i.e., $R_3$ of the precursor of formulas I or II, may react with an electrophilic functional group on another precursor, i.e., the crosslinker, to faun a covalent bond. At least one of the precursors comprises more than two functional groups, so that, as a result of electrophilic-nucleophilic reactions, the precursors combine to form crosslinked macromolecules and/or polymeric products. Such reactions may be referred to as "crosslinking reactions".

In some embodiments, the crosslinking reactions occur in an aqueous solution under physiological conditions. In certain embodiments, the crosslinking reactions occur "in situ", meaning they occur at local sites such as on organs or tissues in a living animal or human body. In still other embodiments, the crosslinking reactions do not release heat of polymerization. In yet other embodiments, the crosslinking reactions lead to gelation within 10 minutes, particularly within 2 minutes, more particularly within one minute, and most particularly within 30 seconds.

Certain functional groups, such as alcohols or carboxylic acids, do not normally react with other functional groups, such as amines, under physiological conditions (e.g., pH 7.2-11.0, 37° C.). However, such functional groups can be made more reactive by using an activating group such as N-hydroxysuccinimide. Several methods for activating such functional groups are known in the art. Some non-limiting activating groups include carbonyldiimidazole, sulfonyl chloride, aryl halides, sulfosuccinimidyl esters, N-hydroxysuccinimidyl ester, succinimidyl ester, epoxide, aldehyde, maleimides, imidoesters and the like. The N-hydroxysuccinimide esters or N-hydroxysulfosuccinimide groups are the most preferred groups for crosslinking of proteins or amine functionalized polymers such as aminoterminated polyethylene glycol ("APEG").

In certain embodiments, each polymer precursor may comprise only nucleophilic or only electrophilic functional groups, so long as both nucleophilic and electrophilic precursors are used in the crosslinking reaction. Thus, for example, in some embodiments a crosslinked polymer may be formed by combining a first polymer precursor displaying the following general formula (III):

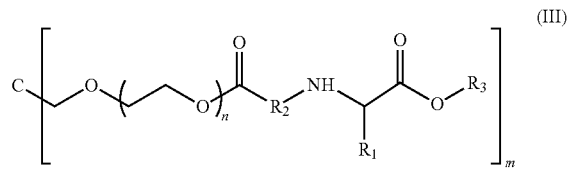

wherein 1≦n≦500,000, and m≧1;
C=represents a core molecule;
$R_1$=—H, or an amino acid side chain;
$R_2$=an alkyl group, a substituted or unsubstituted aryl group, or a peptide; and
$R_3$=an electrophilic functional group,
with a second polymer precursor comprising pendant nucleophilic functional groups, such as amines. On the other hand, in some embodiments a crosslinked polymer may be formed by combining a first polymer precursor displaying the following general formula (IV):

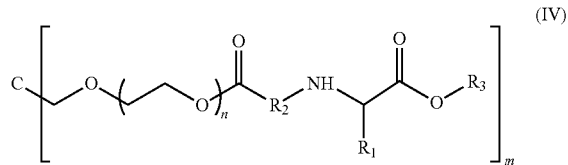

wherein 1≦n≦500,000, and m≧1;

C=represents a core molecule;
$R_1$=—H, or an amino acid side chain;
$R_2$=an alkyl group, a substituted or unsubstituted aryl group, or a peptide; and
$R_3$=a nucleophilic functional group;
with a second polymer precursor comprising pendant electrophilic functional groups, such as —NHS.

Suitable non-limiting examples of nucleophilic functional groups which may be present on any of the polymer precursors or crosslinkers described herein include —$NH_2$, —SH, —OH, —$PH_2$, and —CO—NH—$NH_2$.

Illustrative examples of electrophilic functional groups which may be present on any of the polymer precursors or crosslinkers described herein include, but are not limited to, —$CO_2N(COCH_2)_2$, —$CO_2H$, —CHO, —$CHOCH_2$, —N═C═O, —$SO_2CH$═$CH_2$, —$N(COCH_2)_2$, —ON$(COCH_2)_2$, —S—S—$(C_5H_4N)$, benztriazole, p-nitrophenyl, carbonylimidazole, vinylsulfones, maleimides, N-hydroxysuccinimide esters (NHS), N-hydroxysulfosuccinimide esters (SNHS), and N-hydroxyethoxylated succinimide esters (ENHS).

As shown in Formulas I, II, III, and IV above, "n" refers to the number of repeating units within the precursor structure, "C" represents a core molecule used to form the precursor structure and "m" refers to the number of arms or branches in the precursor structure. Although any number of arms may be suitable for forming the crosslinked polymers described herein, in particularly useful embodiments, "m" may represent from about 1 to about 32 arms in the first polymer precursor. In some embodiments, "m" may represent from about 2 to about 16 arms in the first polymer precursor. In still other embodiments, "m" may represent 4 or 8 arms.

In embodiments wherein "m" is greater than 1, the first polymer precursor may include a core of a multifunctional compound. Some non-limiting examples of multifunctional compounds suitable for forming the core of the first polymer precursor may include glycerol, pentaerythritol, sorbitol and the like. In embodiments, the core molecule may be a branched polymer or a dendrimer.

In some embodiments, "n" may represent from about 1 to about 500,000. In still other embodiments, "n" may represent from about 2 to about 50,000. In still other embodiments, "n" may represent from about 10 to about 20,000.

Figure 2:
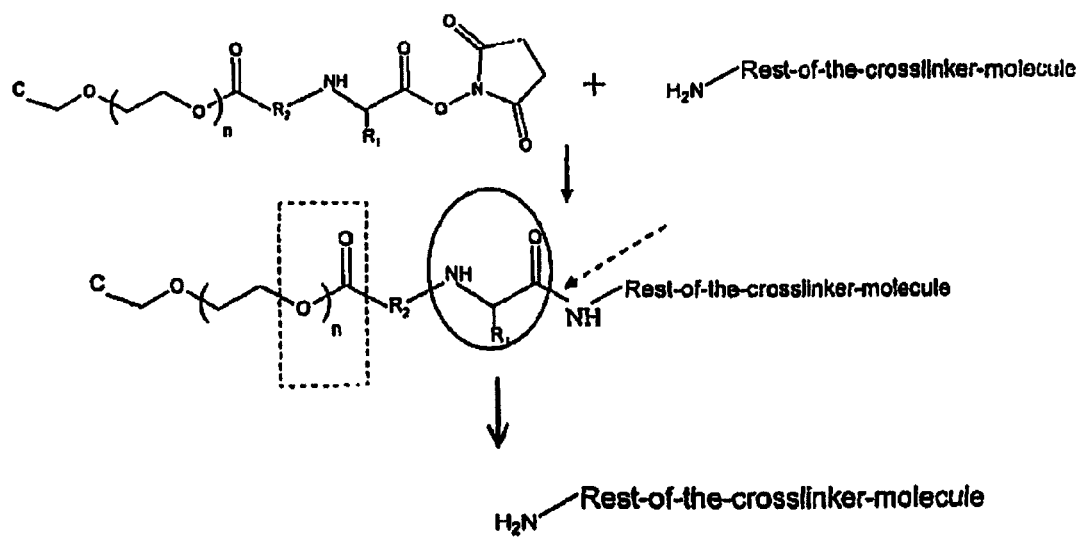
FIG. 2 illustrates the polymerization chemistry of combining first and second polymer precursors to form a crosslinked polymer and the degradation of the crosslinked polymer.

As further depicted in formulas II, III, and IV above, and FIG. 2, each arm of the first polymer precursor includes a first ester group (O—C═O) linked to a functionalized second ester group (O═C—O—$R_3$) via a secondary amine (NH). It is envisioned that the first ester group represents a hydrolytically unstable linkage which may react with water causing the first precursor to separate into two or more components. The secondary amine provides the precursor with a hydrolytically stable linkage which may be stable in water and may not react with water for extended periods of time, potentially indefinitely. The secondary amine may be cleaved through enzymatic and/or non-enzymatic means. It is this cleaving which may allow the second polymer precursor or crosslinker to be released from the polymer in its original and unmodified form during degradation.

The second ester group functionalized with an electrophilic or nucleophilic functional group provides the precursor with the ability to interact or chemically bond with at least one additional polymer precursor or crosslinker via a crosslinking reaction.

In some embodiments, $R_1$ of formulas I, II, III, and IV above may represent at least an amino acid side chain. As shown in formula V, which depicts the general chemical structure of an amino acid, an amino acid has at least one amine and one carboxylic acid functional group as the name implies. The different properties between the wide variety of amino acids result from variations in the structures of different R groups. The R group is often referred to as the amino acid side chain.

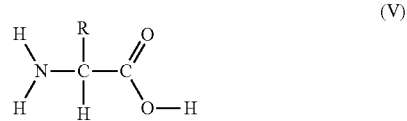

(V)

Amino acid side chains may be polar, non-polar, acidic, basic, or neutral. In certain embodiments, $R_1$ of formulas I, II, III, and IV refers to a side chain of any natural amino acid found in proteins. Some non-limiting examples include, but not limited to, the side chain of one or more of the following amino acids: alanine, serine, leucine, glutamic acid, methionine, cysteine, lysine, asparagine, aspartic acid, glutamine, valine, tryptophan, threonine, phenylalanine, tyrosine, arginine, histidine, 5-hydroxylysine, thyroxine, 3-methylhistidine, methyllysine, trimethyllysine, aminoadipic acid, pyroglutamic acid, phosphothreonine, phosphotyrosine, n-methylarginine, n-acetyllysine, and combinations thereof. In some embodiments, $R_1$ may refer to one of the following: H, $CH_3$, $CH_2$—OH, $CH_2$—$CH(CH_3)_2$, $CH_2$—$CH_2$—$CO_2H$, $CH_2$—$CH_2$—S—$CH_3$, $CH_2$—SH, $CH_2$—$CH_2$—$CH_2$—$CH_2$—$NH_2$, $CH_2$—$CH_2$—CO—$NH_2$, $CH_2$—$CO_2H$, $CH_2$—CO—$NH_2$, $CH(CH_3)_2$, $C_8H_6N_1$—$CH_2$, $CH(OH)CH_3$, $C_6H_5$—$CH_2$, $CH_2$—$C_6H_5$—OH, $CH_2$—$CH_2$—$CH_2$—NH—C(NH)($NH_2$), $CH_2$—$C_3H_3N_2$, $(CH_2)_2$—CH—OH—$CH_2$—$NH_2$, $CH_2$—$(C_6H_2I_2)$—O—$(C_6H_2I_2)$—OH, $CH_2$—$(C_3H_2N_2)$—$CH_3$, $CH_2$—$CH_2$—$CH_2$—$CH_2$—NH—$CH_3$, $CH_2$—$CH_2$—$CH_2$—$CH_2$—N—$(CH_3)_3$, $CH_2$—$CH_2$—$CH_2$—$CO_2H$, CH—$(CH_3)$—O—P—(O)$(OH)_2$, $CH_2$—$C_6H_4$—O—P—(O)$(OH)_2$, $CH_2$—$CH_2$—$CH_2$—NH—C—(NH)(NH—$CH_3$), $CH_2$—$CH_2$—$CH_2$—$CH_2$—NH—C—(O)($CH_3$), $CH_2$—$OPO_3H_2$, and $CH_2$—$CH(CO_2H)_2$.

In other embodiments, $R_1$ may refer to at least one side chain of a natural amino acid not commonly found in proteins. Some non-limiting examples of such natural amino acids include homoserine, homocysteine, sarcosine, aminobutyric acid, betaine, β-alanine, azaserine, 1-lanthionine, 1-phenylserine, 1-chloramphenicol, cycloserine, penicillamine, ornithine, and citrulline. In some embodiments $R_1$ may refer to one of the following: $CH_2$—$CH_2$—OH, $CH_2$—$CH_2$—SH, $CH_2$—O—CO—CH=N=N, $CH_2$—S—CH($NH_2$)($CO_2H$), CH(OH)($C_6H_5$), C(SH)$(CH_3)_2$, $CH_2$—$CH_2$—$CH_2$—$NH_2$, $CH_2$—$CH_2$—$CH_2$—NH—C(O)($NH_2$).

It is envisioned that the side chains of the amino acid representing $R_1$ may correspond to either the D-enantiomer or the L-enantiomer versions of any of the side chains. Although the L-enantiomer version may be more commonly seen in nature, for some applications, the properties of the D-enantiomer version may be more advantageous than the L-enantiomer version. For example, the D-enantiomer may be more stable or allow higher specificity for enzymatic cleavage.

It should be understood that $R_1$, $R_2$, and $R_3$ may be the same or different on each arm of the multiarm embodiments described herein.

$R_2$ of formulas I, II, III, and IV may refer to an aliphatic hydrocarbon, an aromatic-based structure, or a combination thereof. The aliphatic hydrocarbon may represent an alkyl group consisting of between 1 and 20 carbon atoms. For instance, $R_2$ may represent an aliphatic hydrocarbon group derived from oxalic acid, malonic acid, succinic acid, glutaric acid, adipic acid, pimelic acid, azelaic acid, and sebacic acid. The aromatic based-structures may include at least one group derived from an aromatic hydrocarbon, or polyaromatic hydrocarbon (PAH). For instance, $R_2$ may represent an aromatic hydrocarbon group derived from benzoic acid, salicylic acid, or acetylsalicylic acid in some embodiments. Alternatively, $R_2$ may represent a group derived from a polyaromatic hydrocarbon such as benzocyclopropene ($C_7H_6$), benzocyclopropane ($C_7H_8$), benzocyclobutadiene ($C_8H_6$), and benzocyclobutene ($C_8H_8$) to name just a few non-limiting examples.

In still other embodiments, $R_2$ may refer to a peptide chain. In embodiments, $R_2$ is a peptide chain derived from one or more of the known amino acids. In embodiments, $R_2$ is a peptide chain derived from as many as 20 amino acids which may be the same or different. For example, $R_2$ may refer to a peptide chain of 1-50 amino acid residues; in embodiments, 1-25 amino acid residues; in other embodiments 1-10 amino acid residues; in still other embodiments, 1-5 amino acid residues. A peptide chain as the $R_2$ group may aid in the enzymatic cleavage of the amide bond formed by combining the first polymer precursor of formulas I, II, III, and IV with a second polymer precursor or crosslinker.

Turning now to FIG. 1, which depicts one polymerization process of combining a first polymer precursor functionalized with at least one —NHS group with a second polymer precursor, i.e., crosslinker, functionalized with at least one —$NH_2$ group. The process is represented for one arm of a multi-arm polymer precursor. Thus, "C" represents a core of a branched polymer precursor. The resulting polymer includes a hydrolysable link (depicted within the dotted box). Since the first polymer precursor shown in FIG. 1 does not include an amide or secondary amine bond, like the first polymer precursors shown in FIG. 2, the first polymer precursor of FIG. 1 is not susceptible to enzymatic degradation.

As a result, following exposure to water and/or hydrolysis, the crosslinked polymer will degrade via the hydrolysable link. Since the hydrolysable link is positioned downstream from the portion of the crosslinked polymer derived from the crosslinker, such degradation allows for the release of a modified or end-capped crosslinker or second polymer precursor (depicted within the oval of FIG. 1). In other words, following hydrolysis, a portion of the first polymer precursor of FIG. 1 remains attached to the second polymer precursor of FIG. 1 thereby releasing a modified second polymer precursor of FIG. 1.

In FIG. 2, however, which depicts a polymerization process described herein which includes combining a first polymer precursor similar in structure to any of formulas I, II, and III and functionalized with at least one —NHS group with a crosslinker molecule functionalized with at least one —$NH_2$ group. The process is represented for one arm of the polymer precursors. The resulting crosslinked polymer includes a hydrolysable link (depicted within the dotted box in FIG. 2), an amide bond (depicted by the dotted arrow in FIG. 2), and an amino acid residue structure (depicted by oval in FIG. 2). An amino acid residue is a structure which lacks a hydrogen atom of the amino group (—NH—CHR—COOH), or a hydroxyl group of the carboxyl group ($NH_2$—CHR—CO—), or both (—NH—CHR—CO—).

Upon implantation and/or exposure to moisture of bodily fluids the hydrolysable first ester linkage may be subject to rapid hydrolysis and the detachment of a portion of the crosslinked polymer. In addition, the combination of the amide bond and the amino acid residue allow the crosslinked polymer to also be susceptible to enzymatic degradation and/ or non-enzymatic degradation. Since the amide bond is positioned near the portion of the crosslinked polymer derived from the crosslinker, degradation near the amide bond allows for the release of the original crosslinker molecule or second polymer precursor in an unmodified form. For example, following enzymatic degradation at the site of the amide bond (and depicted by the broken arrow in FIG. 2), the crosslinker molecule is released from the crosslinked polymer in an unmodified form (without any addition portions of the first polymer precursor). Degradation of each of the ester linkage and the amide bond may occur sequentially or in parallel depending upon the choice of $R_1$ (amino acid side chain) and/or $R_2$.

Peptide chains, polypeptides, and/or proteins may include a plurality of connected amino acid residues wherein an amide bond is formed between the C-terminus (—CO) portion of a first amino acid residue and the N-terminus (—NH) of a neighboring second amino acid residue. The amino acid residues including at least one amino acid side chain ($R_1$).

Enzymatic or proteolytic cleavage of a peptide chain, polypeptide, or protein typically occurs along the backbone of the peptide chain where the amide bonds have formed. For example, in some embodiments, the first polymer precursor shown in FIG. 2 may include an $R_1$ side chain which represents one of the amino acid side chains of Tryptophan, Tyrosine, Phenylalanine or Leucine. After combining such a first polymer precursor with a second polymer precursor or a crosslinker of FIG. 2, the crosslinked polymer includes an amide bond and an amino acid residue of one of Tryptophan, Tyrosine, Phenylalanine or Leucine. Since the amide bond downstream to the amino acid residue of Tryptophan, Tyrosine, Phenylalanine or Leucine may be cleaved by an enzyme such as Chymotrypsin, such crosslinked polymers may be susceptible to enzymatic cleavage by an enzyme such as Chymotrypsin. Cleavability of the amide bond by Chymotrypsin may allow for the release of the original, unmodified crosslinker depicted in FIG. 2.

Some enzymes have a specificity to certain combinations of amino acid residues. Some enzymes are not as discriminative For example, an enzyme like Trypsin has a specificity only for the amino acid residue immediately upstream to the target amide bond—i.e. an Arginine or Lysine amino acid residue upstream to the target amide bond in a peptide chain, polypeptide or protein. Thus, an enzyme like Trypsin does not discriminate based upon the chemistry downstream of the target amide bond. In embodiments, Trypsin, and other non-discriminating enzymes, may be useful in cleaving the crosslinked polymers described herein, especially in those polymers wherein the amide bond is not formed by the N-terminus of another amino acid residue. For example, in some embodiments, the first polymer precursors of formulas I, II, or III may be combined with a crosslinker like trilysine which includes an N-terminus amine group and multiple side-chain amine groups to form crosslinked polymers which include amide bonds formed on the N-terminus amine group and amide bonds formed on the side chain amine groups. In such instances, non-discriminative enzymes may be used to cleave the crosslinker in an unmodified form and selection of such non-discriminative enzymes may be dependent upon the choice of $_{R1}$ and $_{R2}$ groups in the first polymer precursor of formulas I, II, or III.

As shown in FIG. 2, in some embodiments, the second polymer precursor or crosslinker may be an amine-pendant molecule or compound. Since the amine-pendant compound may be released upon degradation in its original form without modification, a wide variety of amine-pendant therapeutic molecules may be suitable for use in connection with the present disclosure. For instance, the amine-pendant compound may be any molecule which contains at least 2 pendant primary amine groups. Some non-limiting examples include polyamines such as spermidine, spermine, cadaverine, putrescine and the like. In some embodiments, the amine-pendant compound may be a synthetic compound that includes multiple primary amine groups. One non-limiting example of such a synthetic compound includes trilysine. In other embodiments, the amine-pendant compound may include natural materials which include multiple primary amine groups, such as collagen, albumin, chitosan, keratin, elastin, proteins, peptides, amino acids, and the like.

In still other embodiments, the amine-pendant compound may be a therapeutic molecule, such as amine-containing drugs. It should be understood that by "therapeutic molecule" is meant any substance intended for the diagnosis, cure, mitigation, treatment, or prevention of disease in humans and other animals, or to otherwise enhance physical or mental well being. Drug is also intended to include any combinations and alternative forms of the drugs, such as alternative salt forms, free acid forms, free base forms, pro-drugs and the like. The crosslinked polymers and polymer precursors described herein may be used for delivery of biologically active substances generally that have some activity or function in a living organism or in a substance taken from a living organism.

Any amine-containing therapeutic molecule suitable for reaction with the first polymer precursors of formula I, II or III described herein may be used. Some examples include, but are not limited to, drugs which include primary amines such as methamphetamines, dextroamphetamine, dopamine, serotonin, norepinephrine, benzocaine, acyclovir, aminophylline, tetracyclines, choline, histamine, catecholamines, aminoglutethamide, isoniazid, hydralazine, iproniazid, hydrochlorothiazide, chlorothiazide, furosemide, tobramycin, gentamycin, and other aminoglycosides, tetracyclines and combinations thereof. It is envisioned that a plurality of therapeutic agents may be combined with other natural and/or synthetic polymeric materials to form multi-functional linear and/or branched amine-pendant compounds that include multiple primary amine groups.

The crosslinked polymers described herein may be formed in certain embodiments by combining a first polymer precursor of formula I, II or IV, wherein the $R_3$ groups are nucleophilic pendant —$NH_2$ groups, with a crosslinker having pendant electrophilic groups, for example —NHS groups. The resulting crosslinked polymers may contain a hydrolysable first ester linkage (see the dotted box in FIG. 2), an amide bond, and an amino-acid residue (see the oval in FIG. 2) including an amino acid side chain ($R_1$). Upon implantation or exposure to moisture or bodily fluids the first ester linkage may be subject to rapid hydrolysis and the detachment of a portion of the polymer. In addition, the amide bond may be cleaved by enzymatic degradation and/or non-enzymatic degradation. Degradation of each of the ester linkage and the amide bond may occur sequentially or in parallel depending upon the pendant amino-acid residue.

In some embodiments, the second polymer precursor or crosslinker may be a compound which includes multiple pendant —NHS groups. It is envisioned that any suitable compound which includes pendant —NHS groups may be useful in forming the crosslinked polymers described herein.

In embodiments wherein the first polymer precursor follows the formula I, II, or IV, wherein $R_3$ may contain nucleophilic groups, the second polymer precursor or crosslinker may be a drug which includes electrophilic pendant groups. Any suitable drug containing multiple electrophilic functional groups may be used. A non-limiting example includes enalapril which includes multiple pendant carboxylic acids.

Where more than one drug or therapeutic agent may be combined with the first polymer precursors of formulas I, II, III, or IV, it may be beneficial to provide a multi-arm precursor which includes more than one $R_1$ and/or $R_2$ group within the same multi-arm precursor structure. By using different $R_1$ and/or $R_2$ groups, different enzymes may be required to cleave the therapeutic agents from the crosslinked polymers. Thus, a first enzyme may cleave a first therapeutic agent from a first arm of the crosslinked polymer at a faster rate than a second enzyme might cleave a second therapeutic agent of a second arm of the same crosslinked polymer. In such embodiments, each aim of the crosslinked polymer may be tailored to modulate the release rate of one or more of the drugs or therapeutic agents.

Also, in certain embodiments, it is envisioned that the $R_2$ group of at least one arm of the multiarm polymer precursors of formulas I, II, III, or IV may refer to a peptide chain suitable, upon degradation, for cleaving an amide bond formed on the same or different arm of the multiarm crosslinked polymer. For example, an $R_2$ group which represents a peptide chain similar to Chymotrypsin may be made part of at least one arm of the multiarm first polymer precursor of formulas I, II, III, or IV. Such first polymer precursors may also include an $R_1$ representing an amino acid side chain selected from Tryptophan, Tyrosine, Phenylalanine or Leucine (susceptible to enzymatic degradation by Chymotrypsin). In such an embodiment, the degradation of at least one arm of the crosslinked polymers may release the $R_2$ peptide chain and thus release a Chymotrypsin-like peptide chain near the amide bond formed in the crosslinked polymers which contains a pendant $R_1$ amino acid side chain similar to one of Tryptophan, Tyrosine, Phenylalanine or Leucine (which may be susceptible to cleavage by the released Chymotrypsin-like peptide chain). In embodiments, degradation of the crosslinked polymers described herein may be performed by the enzymes found naturally within the body at the site of implantation or may be injected to the site of implantation to speed the process of degradation along. In embodiments, the enzymes or derivatives of enzymes may be carried by or incorporated into the crosslinked polymers.

The first and second polymer precursors or crosslinkers described herein may be combined to form crosslinked polymers suitable as tissue sealants, adhesives, hemostats, coatings on a medical device, drug delivery devices, adhesion-barriers, and/or tissue-fillers. In embodiments, the crosslinked polymers form biodegradable hydrogel materials suitable for implantation. The polymer precursors and/or the crosslinked polymers may be applied directly to tissue or may be applied to a surface of an implantable medical device, such as a stent, mesh, suture, staple, balloon, suture anchor, bone plate, pin, screw, rod, and the like. The polymer precursors and/or the crosslinked polymers may be applied to the tissue or medical device using any suitable method including, but not limited to, dipping, wiping, brushing, spraying, injecting, and pouring.

Figure 3:
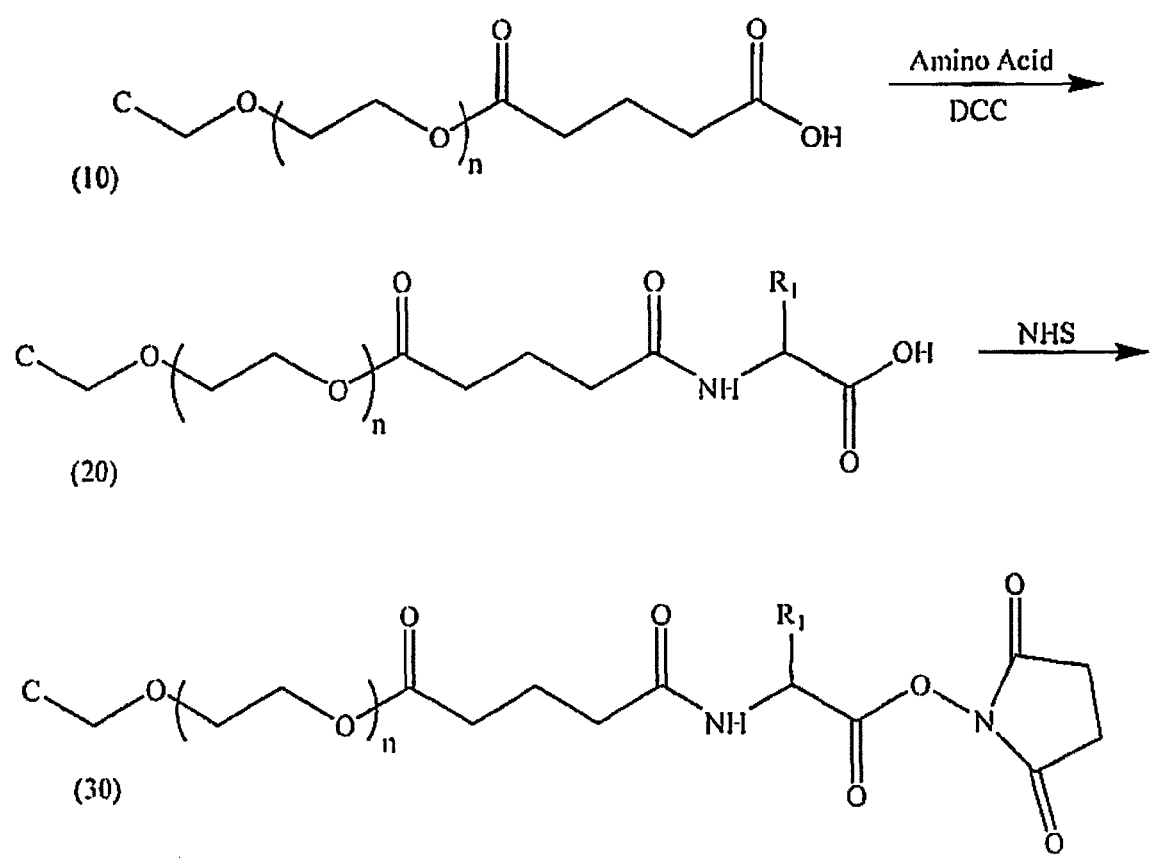
FIG. 3 illustrates one method of synthesizing the polymer precursors described herein.

The first polymer precursors described herein may be formed using any suitable chemical methodology suitable for forming the chemical structures shown in any of the formulas and figures described herein. In some embodiments, the first polymer precursors described herein may be synthesized as depicted in FIG. 3. More specifically, at least one arm of a multi-branched core molecule ("C") selected from any variety of non-toxic polyhydroxy compounds like sugars (xylitol, sorbitol, erythritol), glycerol, pentaerythritol, and trimethylolpropane, may be chain extended using a linear polymer material, such as polyethylene glycol, and an anhydride, such as glutaric anhydride, to form the initial polymer precursor 10 of FIG. 3. Other biocompatible polymer and anhydride materials may be combined with the core molecule to form the initial polymer precursors 10 described herein. For instance the anhydride may be selected from succinic anhydride, malonic anhydride, adipic anhydride, pimelic anhydride, suberic anhydride, azelaic anhydride, and sebacic anhydride. Some other examples of suitable polymers include polyvinylpyrrolidone, polyvinyl alcohols, polyalkylene glycols, and the like. Initial polymer precursor 10 as shown in FIG. 3 may be reacted with dicyclohexylcarbodiimide (DCC) and any amino acid to form intermediate polymer precursor 20. Intermediate polymer precursor 20 may further be reacted with any suitable materials having pendant electrophilic and/or nucleophilic groups, such as those described herein to form first polymer precursors described herein in formulas I-IV. For instance, as depicted in FIG. 3, intermediate polymer precursor 20 may be combined in a manner which produces a pendant —NHS group on the polymer precursor.

Several crosslinked polymers may be produced using the first polymer precursors of formulas I, II, and/or III. The reaction conditions for crosslinking will depend on the nature of the functional groups. In embodiments, the reactions may be conducted in buffered aqueous solutions at pH of about 2 to about 12; in embodiments a pH of about 5 to about 10. Suitable non-limiting examples of buffers may include sodium borate, triethanol amine, sodium phosphate, carbonate, and potassium hydrogen phthalate. Elevated pH may increase the speed of the reactions. In some embodiments, organic solvents such as ethanol or isopropanol may be added to improve the reaction speed or to adjust the viscosity of a given formulation.

In embodiments, at least one of the first and second polymer precursors or crosslinkers may be in particulate form. In such embodiments, the cross-linking reaction may not occur until at least one of the two compounds are exposed to moisture. In some embodiments, the particulate materials may be applied separately or sequentially to a medical device or on living tissue. In other embodiments, the particulate materials may be applied simultaneously to a medical device or tissue.

The crosslinked polymers described above may degrade due to hydrolysis of the ester linkage and enzymatic degradation of the amide bond due to the pendant amino-acid side chain ($R_1$). The degradation of polymers or gels containing synthetic peptide sequences ($R_2$) will depend on the specific enzyme and its concentration. In some cases, a specific enzyme may be added during the crosslinking reaction to accelerate the degradation process.

Aqueous solutions of the polymer precursors or crosslinkers described herein may be made just before the crosslinking reaction, particularly when the electrophilic groups include —NHS groups.

The crosslinking density of the resultant crosslinked polymers may be controlled by the overall molecular weight of the precursors or crosslinkers, and the number of functional groups available per molecule. A lower molecular weight precursor, such as about 600, will give a much higher crosslinking density as compared to a higher molecular weight precursor, such as about 10,000. In some embodiments, higher molecular weight polymer precursors may be used. In other embodiments, first polymer precursors of more than 3000 may be used so as to obtain elastic gels.

In many applications, the crosslinked polymers typically will be formed "in situ" at a surgical site in the body. The various methodologies and devices for performing "in situ" gelation, developed for other adhesive or sealant systems such as fibrin glue or sealant applications, may be used with the crosslinked polymers of this invention. Thus, in one embodiment, an aqueous solution of a freshly prepared amine-pendant compound (e.g., trilysine in a borate buffer solution at pH 9.5) and a first polymer precursor of formulas I, II, or III (e.g., 4 arm PEG of molecular weight 20,000 daltons, extended with ester linkages, terminated with electrophilic NHS end groups, and including secondary amines positioned therebetween) are co-sprayed on to tissue using an air assisted sprayer such that the two fluid streams mix in the air and at the site of application to form a crosslinked biodegradable hydrogel that is capable of adhering to tissue within seconds. The two solutions may be applied simultaneously or sequentially. In some embodiments, it is preferred to apply the precursor solutions sequentially so as to "prime" the tissue, resulting in improved adherence of the crosslinked polymer to the tissue. Where the tissue is primed, the first polymer precursor may be applied to the tissue first, followed by the amine-pendant compound.

One may use specialized devices to apply the two compounds, such as an adhesive sprayer or such as those described in U.S. Pat. Nos. 4,874,368; 4,631,055; 4,735,616; 4,359,049; 4,978,336; 5,116,315; 4,902,281; 4,932,942; Published PCT Patent Application No. WO 91/09641; and R. A. Tange, "Fibrin Sealant" in *Operative Medicine: Otolaryngology*, volume 1 (1986), the disclosures of which are herein incorporated by reference.

In embodiments, the polymer precursors described herein may be stored and sterilized in separate containers to prevent premature cross-linking from occurring. In some embodiments, the polymer precursors described herein may be stored and sterilized in the same container wherein the cross-linking is prevented from occurring by the use of buffers and/or changes in pH.

It is envisioned that kits for delivering the materials to the site of implantation may be designed. The kits may include a first composition which includes at least one of the first polymer precursors described herein and a second composition which includes at least one of the second polymer precursors described herein. The first and second compositions may be stored in the same or separate container(s) and the kit includes a means for delivering the first and second compositions to the site of implantation and/or the site of application on a medical device. Suitable delivery devices include, but are not meant to be limited to, one or more surgical syringes, double-barrel syringes, or the specialized devices described above, i.e., an adhesive sprayer. Mixture of the materials which form the crosslinked polymers described herein may occur immediately prior to, during or after implantation.

It will be understood that various modifications may be made to the embodiments disclosed herein. For example, the $R_1$ and $R_2$ portions of the polymer precursors described herein may be chemically connected to one another to form side chains which represent cyclic amino acids, such as proline, and hydroxyproline. Thus, those skilled in the art will envision other modifications within the scope and spirit of the claims.

What is claimed is:

1. A polymer precursor comprising a formula

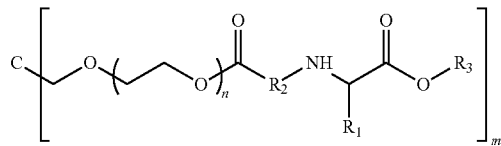

wherein $1 \leq n \leq 500{,}000$, and $m \geq 2$;
C=represents a core molecule;
$R_1$=—H, or an amino acid side chain;
$R_2$=an alkyl group; and
$R_3$=an electrophilic functional group selected from the group consisting of —$CO_2N(COCH_2)_2$, —$CO_2H$, —CHO, —$CHOCH_2$, —N=C=O, —$SO_2CH$=$CH_2$, —$N(COCH_2)_2$, and —S—S—($C_5H_4N$), or a nucleophilic functional group selected from the group consisting of —$NH_2$, —SH, —OH, —$PH_2$, and —CO—NH—$NH_2$.

2. The polymer precursor of claim 1, wherein $R_1$ comprises an amino acid side chain selected from the group consisting of $CH_3$, $CH_2$—OH, $CH_2$—CH($CH_3$)$_2$, $CH_2$—$CH_2$—$CO_2H$, $CH_2$—$CH_2$—S—$CH_3$, $CH_2$—SH, $CH_2$—$CH_2$—$CH_2$—$CH_2$—$NH_2$, $CH_2$—$CH_2$—CO—$NH_2$, $CH_2$—$CO_2H$, $CH_2$—CO—$NH_2$, CH($CH_3$)$_2$, $C_8H_6N_1$—$CH_2$, CH(OH)$CH_3$, $C_6H_5$—$CH_2$, $CH_2$—$C_6H_5$—OH, $CH_2$—$CH_2$—$CH_2$—NH—C(NH)($NH_2$), $CH_2$—$C_3H_3N_2$, ($CH_2$)$_2$—CH—OH—$CH_2$—$NH_2$, $CH_2$—($C_6H_2I_2$)—($C_6H_2I_2$)—OH, $CH_2$—($C_3H_2N_2$)—$CH_3$, $CH_2$—$CH_2$—$CH_2$—$CH_2$—NH—$CH_3$, $CH_2$—$CH_2$—$CH_2$—$CH_2$—N—($CH_3$)$_3$, $CH_2$—$CH_2$—$CH_2$—$CO_2H$, CH—($CH_3$)—O—P—(O)(OH)$_2$, $CH_2$—$C_6H_4$—O—P—(O)(OH)$_2$, $CH_2$—$CH_2$—$CH_2$—NH—C—(NH)(NH—$CH_3$), $CH_2$—$CH_2$—$CH_2$—NH—C—(O)($CH_3$).

3. The polymer precursor of claim 1, wherein $R_1$ comprises a natural amino acid side chain not found in proteins selected from the group consisting of $CH_2$—$CH_2$—OH, $CH_2$—$CH_2$—SH, $CH_2$—O—CO—CH=N=N, $CH_2$—S—CH($NH_2$)($CO_2H$), CH(OH)($C_6H_5$), C(SH)($CH_3$)$_2$, $CH_2$—$CH_2$—$CH_2$—$NH_2$, $CH_2$—$CH_2$—$CH_2$—NH—C(O)($NH_2$).

4. The polymer precursor of claim 1, wherein $R_2$ comprises a $C_1$-$C_{20}$ alkyl group.

5. The polymer precursor of claim 1, wherein the core molecule is selected from the group consisting of glycerol, pentaerythritol and sorbitol.

6. The polymer precursor of claim 1, wherein the core molecule comprises pentaerythritol.

* * * * *